(12) United States Patent
Stone et al.

(10) Patent No.: US 6,596,996 B1
(45) Date of Patent: Jul. 22, 2003

(54) OPTICAL SPECTRAL REFLECTANCE SENSOR AND CONTROLLER

(75) Inventors: Marvin L. Stone, Stillwater, OK (US); Duane Needham, Stillwater, OK (US); John B. Solie, Stillwater, OK (US); William R. Raun, Stillwater, OK (US); Gordon V. Johnson, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 09/912,077

(22) Filed: Jul. 24, 2001

(51) Int. Cl.$^7$ ............................................. G01N 21/00
(52) U.S. Cl. ............................ 250/341.8; 250/341.1; 250/358.1
(58) Field of Search .................... 250/340, 341.1, 250/341.8, 339.01, 339.05, 339.11, 358.1; 47/1.7

(56) References Cited

U.S. PATENT DOCUMENTS

| | | |
|---|---|---|
| 3,910,701 A | 10/1975 | Henderson et al. ........... 356/39 |
| 5,144,767 A | 9/1992 | McCloy et al. ............... 47/1.7 |
| 5,222,324 A | 6/1993 | O'Neall et al. ............... 47/1.7 |
| 5,296,702 A | 3/1994 | Beck et al. .................. 250/226 |
| 5,389,781 A | 2/1995 | Beck et al. .................. 250/226 |
| 5,507,115 A | 4/1996 | Nelson ......................... 47/1.7 |
| 5,555,464 A | 9/1996 | Hatlestad |
| 5,585,626 A | 12/1996 | Beck et al. .............. 250/222.1 |
| 5,606,821 A | 3/1997 | Sadjadi et al. ................ 47/1.7 |
| 5,621,460 A | 4/1997 | Hatlestad et al. |
| 5,661,817 A | 8/1997 | Hatlestad et al. |
| 5,763,873 A | 6/1998 | Beck et al. ............. 250/214 B |
| 5,764,819 A | 6/1998 | Orr et al. |
| 5,768,823 A | 6/1998 | Nelson ......................... 47/1.7 |
| 5,789,741 A | 8/1998 | Kinter et al. |
| 5,793,035 A | 8/1998 | Beck et al. .............. 250/222.1 |
| 5,809,440 A | 9/1998 | Beck et al. .................... 701/50 |
| 5,833,144 A | 11/1998 | Kinter ......................... 239/462 |
| 5,837,997 A | 11/1998 | Beck et al. ............. 250/227.11 |
| 5,878,356 A | 3/1999 | Garrot, Jr. et al. |
| 5,999,650 A | 12/1999 | Ligon |
| 6,062,496 A | 5/2000 | Kinter ......................... 239/462 |
| 6,160,902 A | 12/2000 | Dickson et al. |
| 6,178,253 B1 * | 1/2001 | Hendrickson et al. ....... 382/110 |
| 6,212,824 B1 | 4/2001 | Orr et al. |
| 6,366,681 B1 | 4/2002 | Hutchins |
| 6,393,927 B1 | 5/2002 | Biggs et al. |
| 6,444,975 B1 | 9/2002 | Reusch |

OTHER PUBLICATIONS

Patchen Weed Seeker™ PhD1620 Brochure, Undated.
Patchen Weed Seeker™ PhD600 Brochure, Undated.
J.B. Wilkerson, Ruixiu Sui, W.E. Hart, D.E. Howard, "Development of a Variable–Nitrogen Applicator Spectral Reflectance Characteristics of Cotton Plants," 1998 Proceedings Beltwide Cotton Conferences, San Diego, CA, Jan. 1998, vol. 1, pp. 439–443.
Ruixiu Sui, J.B. Wilkerson, W.E. Hart, and D.D. Howard, "Integration of Neural Networks With a Spectral Reflectance Sensor to Detect Nitrogen Deficiency in Cotton," ASAE Annual International Meeting, Orlando, FL, Jul., 1998.

* cited by examiner

*Primary Examiner*—Constantine Hannaher
*Assistant Examiner*—Timothy Moran
(74) *Attorney, Agent, or Firm*—Fellers, Snider, Blankenship, Bailey & Tippens, P.C.

(57) ABSTRACT

A spectral reflectance sensor including: a light source for emitting a modulated beam of red light; a light source for emitting a modulated beam of near infrared light; a receiver for receiving reflected light produced by either the red source or the near infrared source; a receiver for receiving incident light from either the red source or the infrared source; a signal conditioner responsive to the modulation such that the signals produced by the receivers in response to reflected and incident light from the source can be discriminated from signals produced by ambient light; and a microprocessor having an input such that the microprocessor can determine the intensities of incident red light, reflected red light; incident near infrared light; and reflected near infrared light. From these intensities, and by knowing the growing days since emergence or planting, the sensor can calculate the mid-growing season nitrogen fertilizer requirements of a plant.

7 Claims, 8 Drawing Sheets

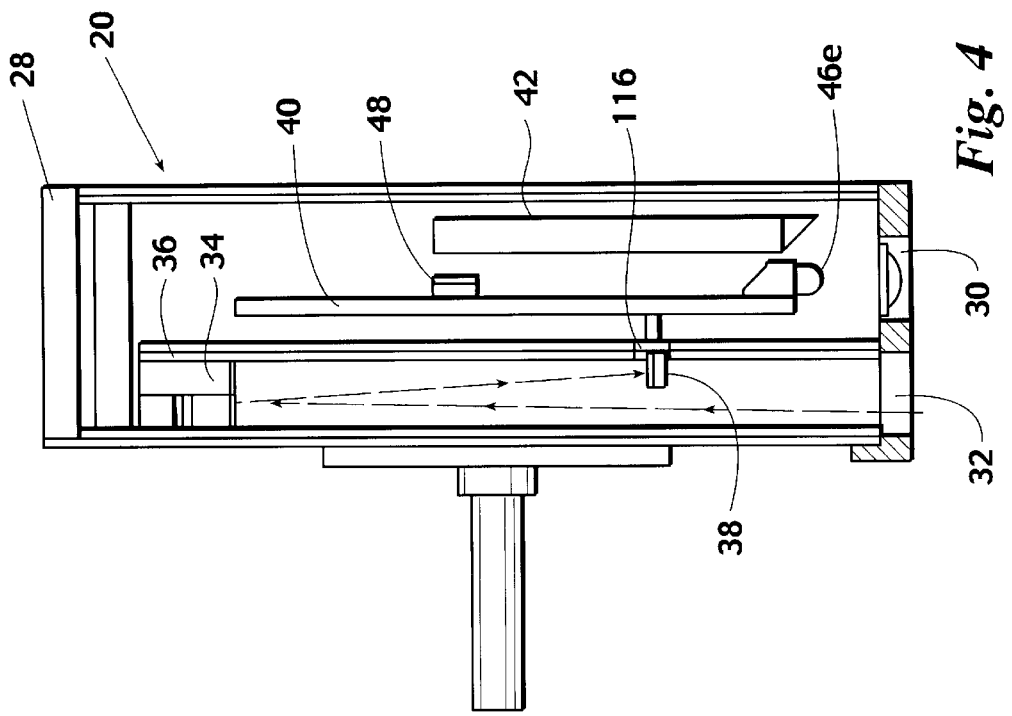
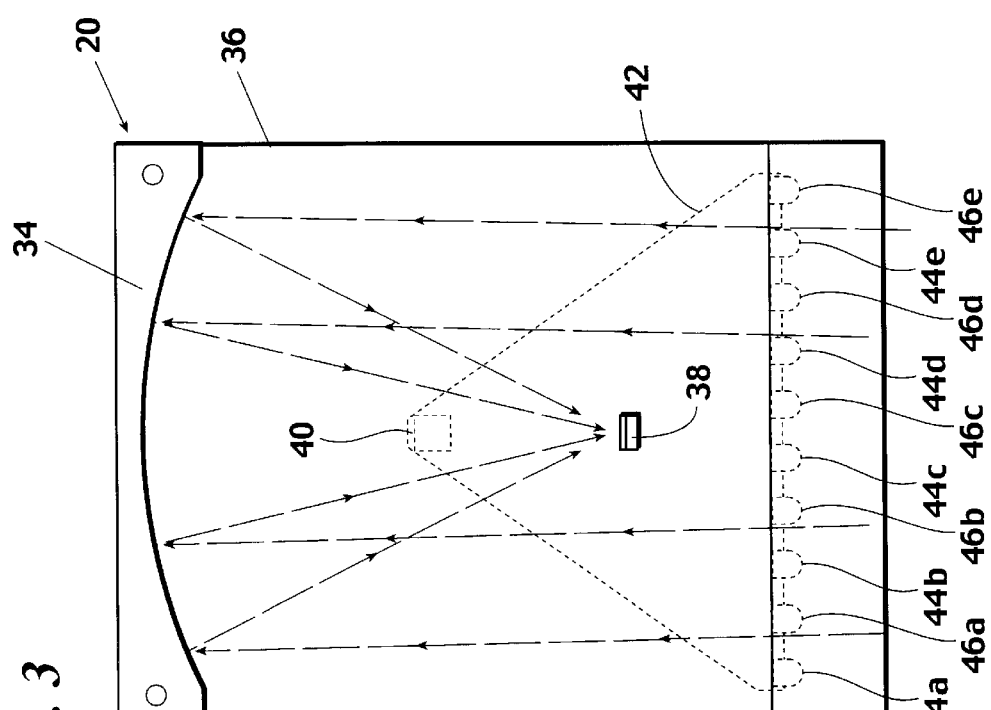

OPTICAL SPECTRAL REFLECTANCE SENSOR AND CONTROLLER

BACKGROUND OF THE INVENTION

1. Field of the Invention

This invention relates generally to a sensor for use in precision farming. More particularly, but not by way of limitation, the present invention relates to an optical spectral reflectance sensor and controller for use in a site specific fertilization system.

2. Background

"Precision farming" is a term used to describe the management of intrafield variations in soil and crop conditions. "Site specific farming", "prescription farming", and "variable rate application technology" are sometimes used synonymously with precision farming to describe the tailoring of soil and crop management to the conditions at discrete, usually contiguous, locations throughout a field. The size of each location depends on a variety of factors, such as the type of operation performed, the type of equipment used, the resolution of the equipment, as well as a host of other factors. Generally speaking, the smaller the location size, the greater the benefits of precision farming, at least down to approximately one square meter.

Typical precision farming techniques include: varying the planting density of individual plants based on the ability of the soil to support growth of the plants; and the selective application of farming products such as herbicides, insecticides, and, of particular interest, fertilizer.

In contrast, the most common farming practice is to apply a product to an entire field at a constant rate of application. The rate of application is selected to maximize crop yield over the entire field. Unfortunately, it would be the exception rather than the rule that all areas of a field have consistent soil conditions and consistent crop conditions. Accordingly, this practice typically results in over application of product over a portion of the field, which wastes money and may actually reduce crop yield, while also resulting in under application of product over other portions of the field, which may also reduce crop yield.

Perhaps even a greater problem with the conventional method is the potential to damage the environment through the over application of chemicals. Excess chemicals, indiscriminately applied to a field, ultimately find their way into the atmosphere, ponds, streams, rivers, and even the aquifer. These chemicals pose a serious threat to water sources, often killing marine life, causing severe increases in algae growth, leading to eutrophication, and contaminating potable water supplies.

Thus it can be seen that there are at least three advantages to implementing precision farming practices. First, precision farming has the potential to increase crop yields, which will result in greater profits for the farmer. Second, precision farming may lower the application rates of seeds, herbicides, pesticides, and fertilizer, reducing a farmer's expense in producing a crop. Finally, precision farming will protect the environment by reducing the amount of excess chemicals applied to a field which may ultimately end up in a pond, stream, river, and/or other water source.

Predominately, precision farming is accomplished by either: 1) storing a prescription map of a field wherein predetermined application rates for each location stored for later use; or 2) by setting application rates based on real-time measurements of crop and/or soil conditions. In the first method, a global positioning system (GPS) receiver, or its equivalent, is placed on a vehicle. As the vehicle moves through the field, application rates taken from the prescription map are used to adjust variable rate application devices such as spray nozzles. A number of difficulties are associated with the use of such a system, for example: due to the offset between the GPS receiver and the application element, the system must know the exact attitude of the vehicle in order to calculate the precise location of each nozzle or application element, making it difficult to accurately and precisely treat the target area; soil and plant conditions must be determined and a prescription developed and input prior to entering the field; and resolving a position with the requisite degree of accuracy requires relatively expensive equipment.

In the latter method, a sensor is used to detect particular soil and plant conditions as the application equipment is driven through the field. The output of the sensor is then used to calculate application rates and adjust a variable rate applicator in real time. Since the physical relationship between the sensor and the applicator is fixed, the problems associated with positional based systems (i.e., GPS) are overcome. In addition, the need to collect data prior to entering the field is eliminated, as is the need for a prescription map.

The limiting factor, thus far, in the later method has been the degree to which sensors are available which provide meaningful information concerning conditions within the field. For example, U.S. Pat. No. 5,585,626 issued to Beck et. al., and U.S. Pat. No. 5,763,873, likewise issued to Beck et al., discloses a sensor which detects plants in a field so that herbicide may be selectively applied to unwanted, plants. Unfortunately, these devices discriminate only between soil and a plant. Thus, as a sprayer is passed over areas where there should only be bare soil, herbicide will automatically be applied to any plants detected. In practice, the sensors of the Beck '626 and '873 patents have proven to be temperature sensitive and thus, to require nearly continuous monitoring and regular re-adjustment while being used. Furthermore, due to the nature of these devices, the distance between the sensor and the ground must be maintained with a relatively high degree of precision. Another limitation is that presently, no such sensor exists for the application of nitrogen fertilizer.

Thus it is an object of the present invention to provide a sensor for use in precision farming which provides an output indicative of one or more growing conditions over a relatively small area, which may be used for the selective application of a farming product or used in the development of a prescription map.

SUMMARY OF THE INVENTION

The present invention provides a sensor for use in precision farming which satisfies the needs and overcomes the problems discussed above. The sensor measures the reflectance of a target at one or more wavelengths of light and, based on known reflectance properties of the target, produces an output indicative of the need for a given farm product.

In a preferred embodiment, the sensor comprises: a light emitter which provides one or more light sources, each source producing light at a specific wavelength; a modulator for modulating each light source at a particular frequency, a reflected light receiver for receiving, detecting, and discriminating each wavelength of light; a direct receiver for receiving light directly from each source; and a processor for gathering information from the receivers and processing such information to determine reflectance of a plant and to determine the need for a given product based on the reflectance information.

The reflectance properties of a target are known to vary based on the amount of nitrogen available to the plant. By observing the reflected light, at particular wavelengths, preferably in the ranges of red and near infrared, and the intensity of the light source at the same wavelengths, it is possible to predict, with a reasonable degree of certainty, the expected crop yield with the present level of available nitrogen and the maximum crop yield if an ideal amount of nitrogen fertilizer is added. This information may be used in real time to control a variable rate applicator for applying a mid-growing season nitrogen fertilizer or, alternatively, used to develop a prescription map for later application of mid-growing season nitrogen fertilizer to a field. Although the inventive sensor could be easily adjusted for any particular target size, the preferred embodiment allows precision farming of sites having an area of approximately four square feet.

Another feature of the inventive device is that the accuracy of the resulting measurement is relatively independent of the height of the sensor above the ground. Thus, as a vehicle equipped with the sensor moves through a field, the output of the sensor is consistent regardless of the terrain and its effect on the height of the sensor.

Further objects, features, and advantages of the present invention will be apparent to those skilled in the art upon examining the accompanying drawings and upon reading the following description of the preferred embodiments.

BRIEF DESCRIPTION OF THE DRAWINGS

FIG. 3 provides a cutaway back view of the spectral reflectance sensor.

FIG. 4 provides a cutaway side view of the spectral reflectance sensor.

DETAILED DESCRIPTION OF THE PREFERRED EMBODIMENT

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Figure 1:
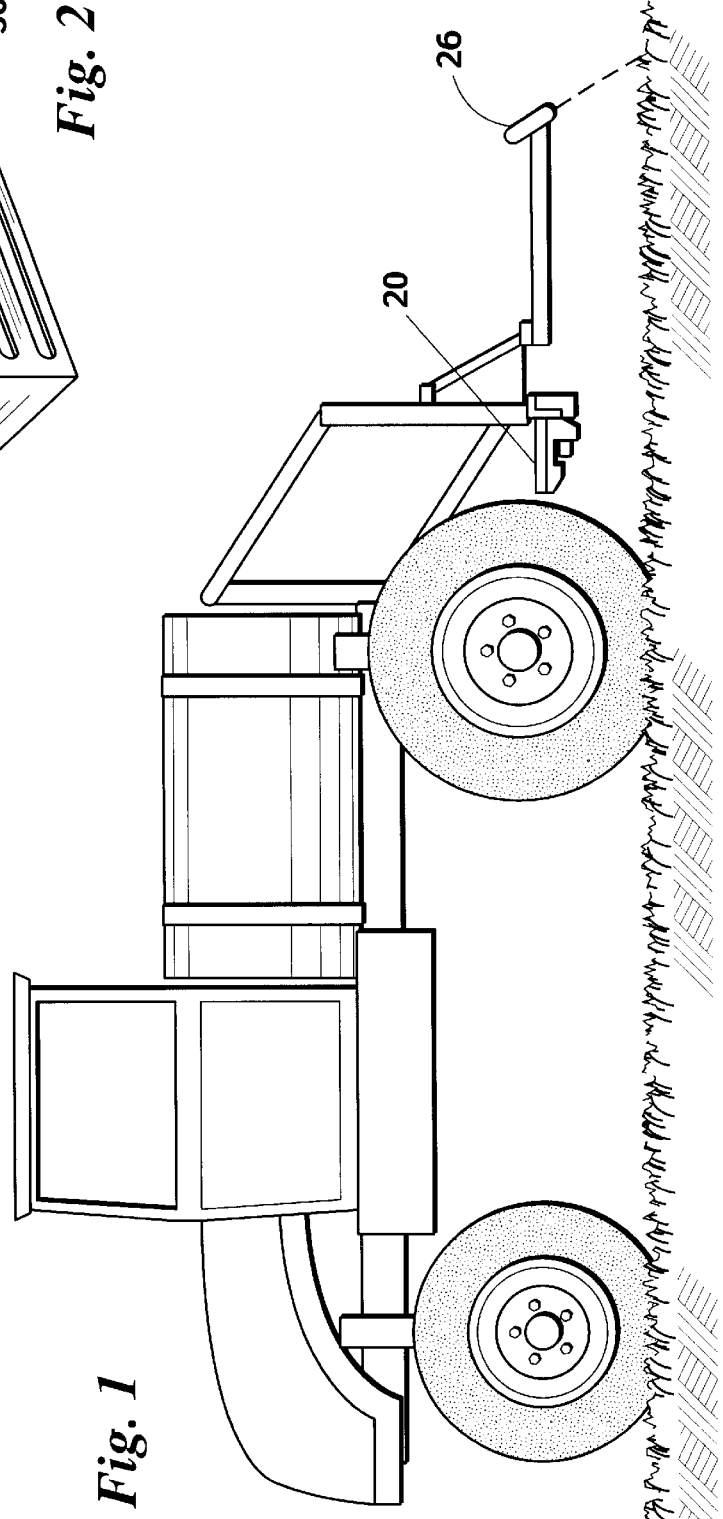
FIG. 1 provides a side view of a farming vehicle having an inventive spectral reflectance sensor mounted thereon.
Figure 1A:
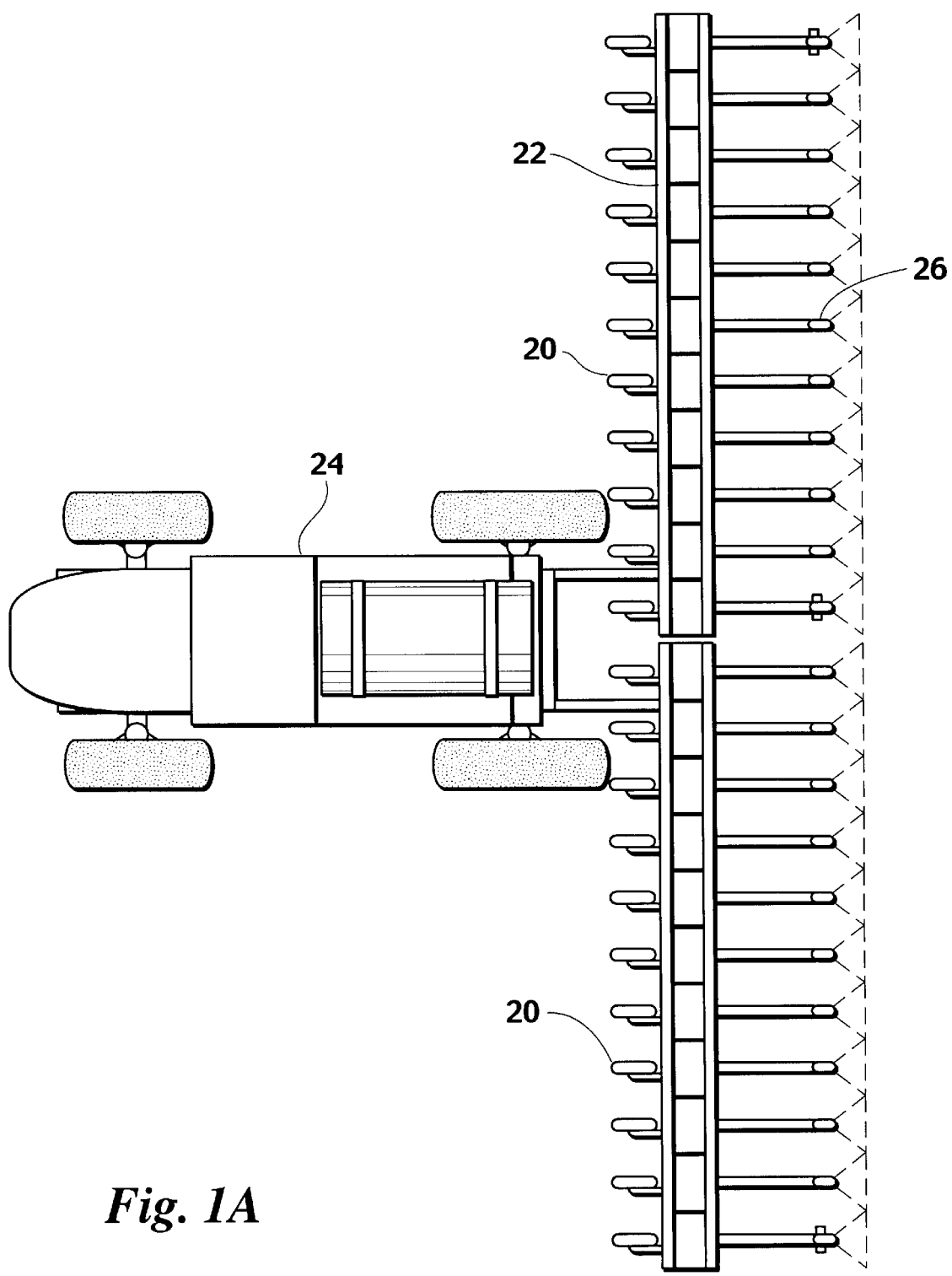
FIG. 1A provides a top view of the farming vehicle showing a typical arrangement of the inventive sensors in use to control the selective application of a farm product.

Referring now to the drawings, wherein like reference numerals indicate the same parts throughout the several views, a preferred embodiment of the inventive reflectance sensor 20 is shown in its general environment in FIGS. 1 and 1A. In one application, a plurality of sensors, of which sensors 20 are representative, are disposed along boom 22 at substantially equal spacings. Preferably, boom 22 extends laterally from vehicle 24. Spray nozzles, of which nozzle 26 is representative, are also disposed along boom 22 preferably such that a nozzle 26, or group of nozzles, corresponds to each sensor 20. As the vehicle 24 travels along a crop row, boom 22 projects over the plants such that each sensor 20 evaluates the plant or plants in its immediate view, determines the extent to which nitrogen fertilizer is needed, and controls the rate of application of fertilizer through its corresponding nozzle 26.

Figure 2:
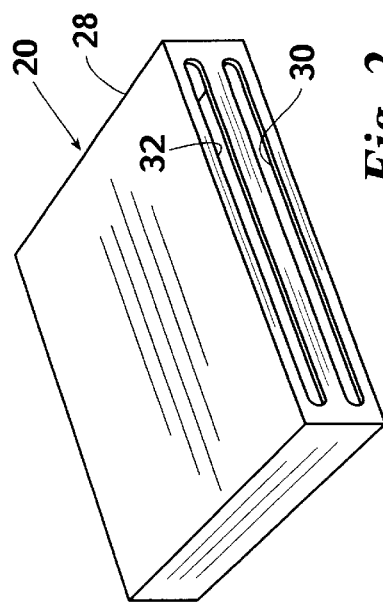
FIG. 2 provides a perspective view of a preferred embodiment of the spectral reflectance sensor.

Referring next to FIGS. 2 and 3, reflectance sensor 20 comprises: a housing 28; an emitter lens 30 located on the bottom of housing 28; and a receiver lens 32 likewise located on the bottom of housing 28. Preferably lens 32 and lens 30 will be selected such that the light emitted by sensor 20 will illuminate an area of consistent size and shape over a range of heights above the ground and likewise, sensor 20 will detect the reflected light consistently from approximately the same area as is illuminated by the sensor.

As best seen in FIGS. 3 and 4, housed within housing 28, sensor 20 further includes parabolic reflector 34 secured to divider 36, for focusing light received through receiver lens 32 onto photodetector 38. Reflected light photodetector 38 projects through aperture 116 in divider 36 to receive only light received through receiver lens 32.

While not critical to the operation of the present sensor, it should be noted that in the preferred embodiment, the light source LEDs 44a–e and 46a–e are located in close physical proximity to the detector 38. This feature minimizes the effect of sensor height on the location of the illuminated surface relative to the field-of-view of the detector 38. In addition, the LED's 44a–e and 46a–e are distributed along a row and, furthermore, the light is projected through a cylindrical lens 30 oriented parallel with the row of LEDs 44a–e and 46a–e to restrict the spread of light in the direction of travel to further minimize the effects of variations in sensor height. Finally, the receiver employs a parabolic reflector 34 with the detector 38 located at the point of focus of the reflector 34 to establish a field-of-view of the detector 38 which is relatively independent of sensor height. Preferably the reflector 34 is in the form of an offset section of a 3-dimensional paraboloid such that detector 38 may be located outside of the field-of-view. This construction results in a sensor which produces consistent results relatively independent of sensor height, particular when compared to prior art sensors.

Located on the opposite side of divider 36, sensor 20 includes circuit board 40 and light pipe 42. Circuit board 40 includes a first light source for producing red light made up of a row of LEDs, 44a–e which are positioned to project light downward through lens 30; and a second light source for producing light in the near infrared range made up of a row of LEDs 46a–e, preferably arranged such that LEDs 44a–e and 46a–e are aligned in a row wherein adjacent LEDs alternate between red and near infrared. Preferably, LEDs 44a–e produce red light having a wavelength of approximately 670 nanometers while LEDs 46a–e produce light in the near infrared range ("NIR"), having a wavelength of approximately 780 nanometers. Light pipe 42 receives and collects incident light from LEDs 44a–e and 46a–e and transmits such light to photodetector 48. Detector 48 thus provides a means for directly measuring the intensity of the light produced by LEDs 44a–e and 46a–e. Since light pipe 42 collects light from all of the LEDs 44a–e and 46a–e, the sensor can measure true reflectance from its field-of-view. In addition, by storing a baseline intensity in nonvolatile memory, the sensor can determine when an LED fails based on a reduced intensity of incident light.

Figure 5:
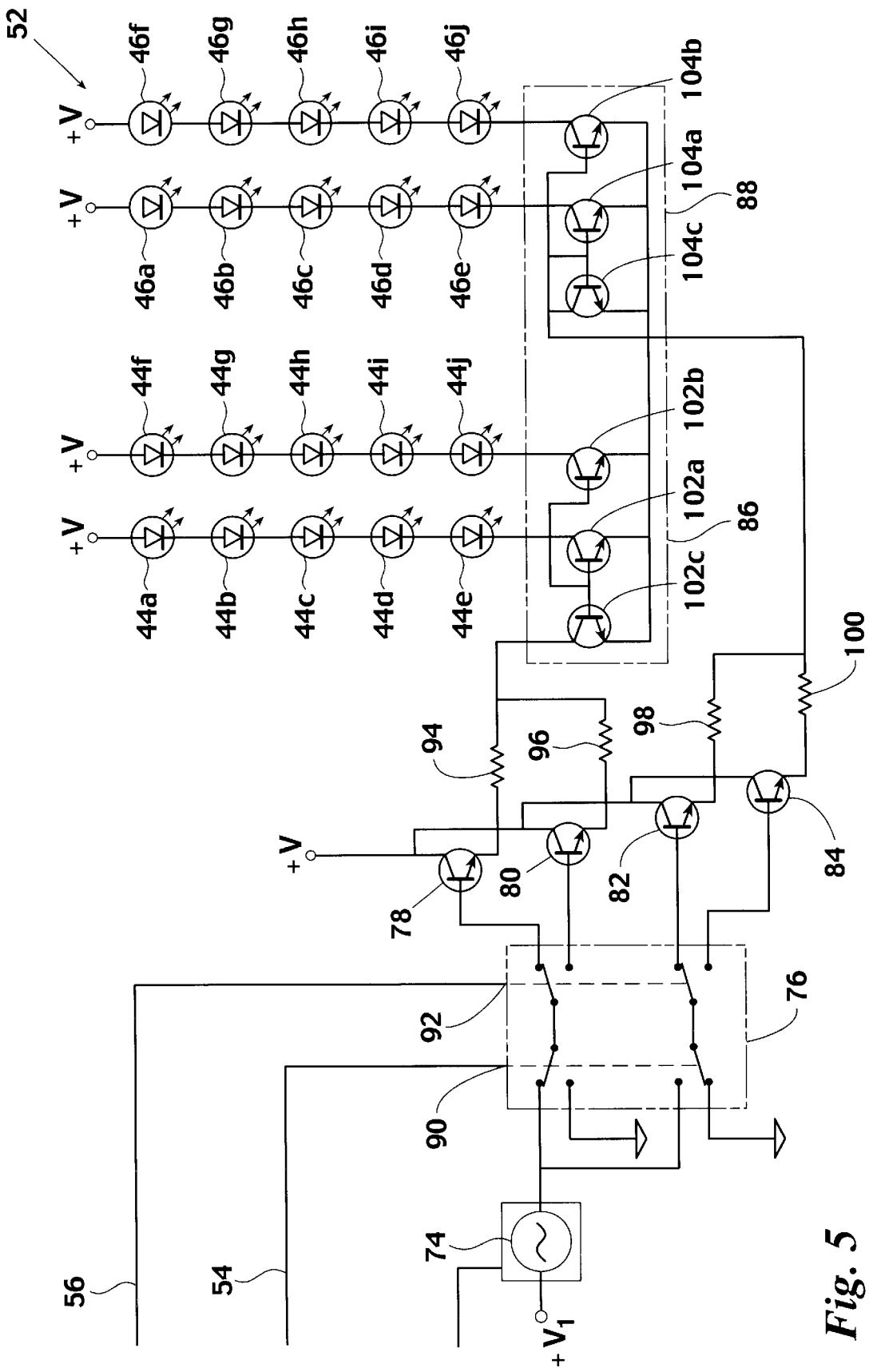
FIG. 5 provides a schematic representation of a preferred emitter circuit as employed in the inventive sensor.
Figure 6:
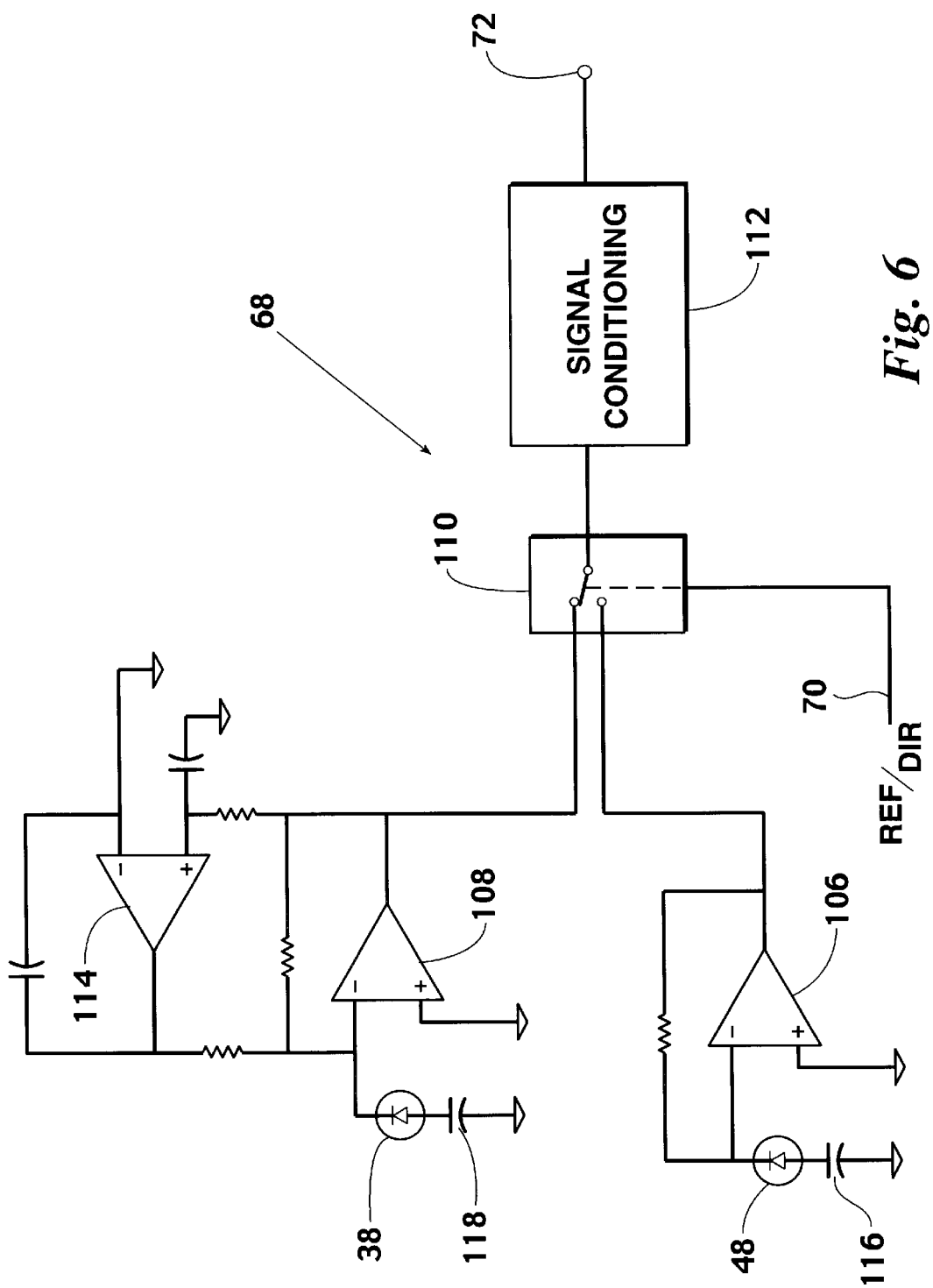
FIG. 6 provides a block diagram of a preferred receiver circuit employed in the inventive sensor.
Figure 7:
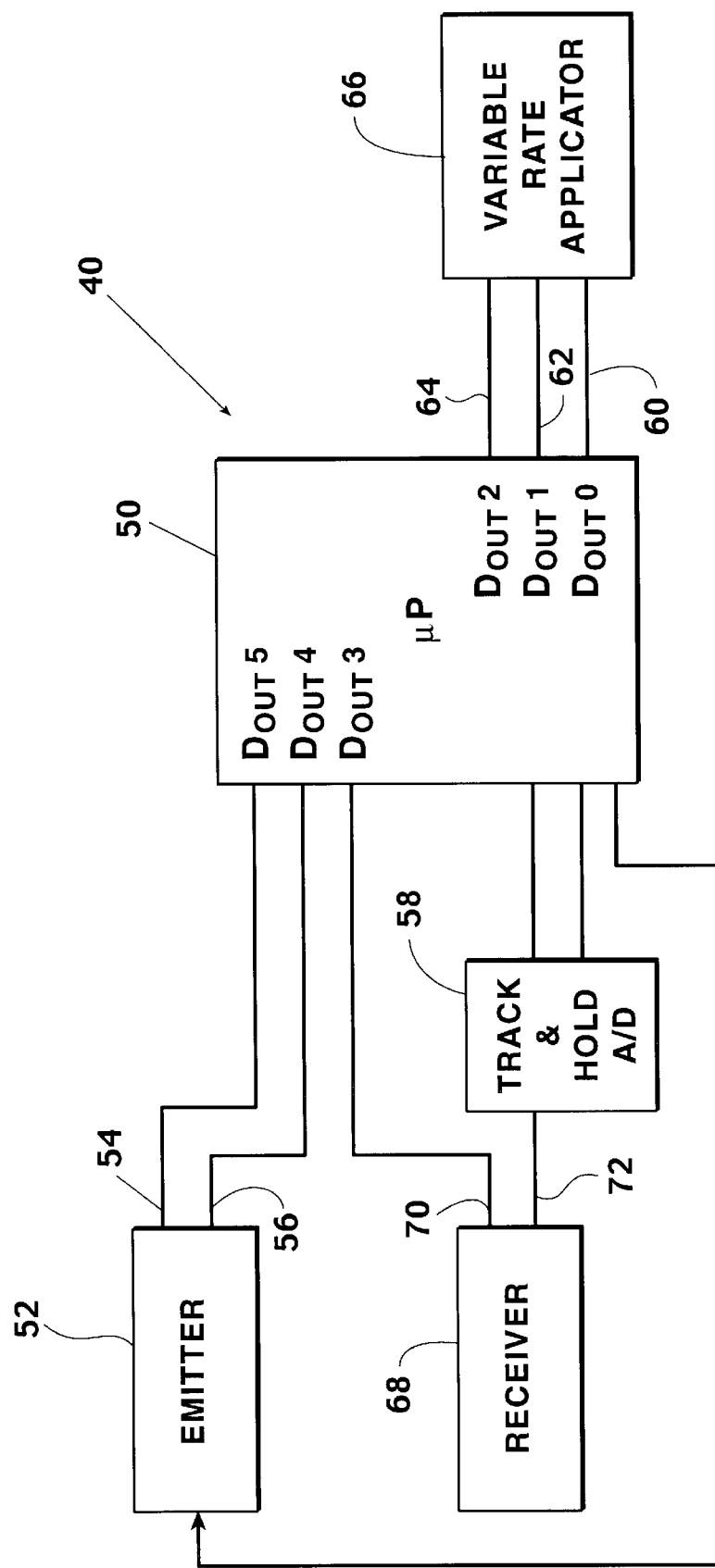
FIG. 7 provides a block diagram of the preferred circuitry of the circuit board employed in the inventive sensor.

The circuitry of circuit board 40 is shown in FIGS. 5–7. Beginning with FIG. 7, circuit board 40 includes: microprocessor 50; an emitter circuit 52 having a color input 54 and an intensity input 56; a receiver circuit 68 having an input 70 to select between the signal representing the light striking the reflected light photodetector 38 or the signal representing the light striking the direct photodetector 48, and an analog output 72 which is connected to track and hold analog to digital converter 58. In the preferred embodiment, analog to digital converter 58 provides 12 bits of resolution although analog to digital converters of more or less resolution are suitable for use with the present invention. Microprocessor 50 includes outputs 60, 62, and 64 for driving variable rate applicator 66 which will be discussed in more detail, hereinbelow.

The term "microprocessor" is used in its broadest sense to describe any computing device. In addition to devices generically known as microprocessors, the term includes, by way of example and not limitation, microcontrollers, RISC devices, ASIC devices manufactured to provide logical and mathematical functions, FPGA devices programmed to provide logical and mathematical functions, computers made up of a plurality of integrated circuits, and the like.

Referring next to FIG. 5, preferably emitter 52 comprises: an oscillator 74 which produces a periodic output having a frequency of approximately 40 kilohertz; switch 76; amplifiers 78, 80, 82, and 84; LEDs 44a–e and 46a–e; and current mirrors 86 and 88.

Analog switch 76 includes a color input 54 and an intensity input 56. When color input 54 is at a first binary state, the output of oscillator 74 is directed to either amplifier 78 or amplifier 80, depending on the state of intensity input 56. When color input 54 is at its second binary state, the output of oscillator 74 is instead directed to either amplifier 82 or amplifier 84, likewise depending on the state of intensity input 56. Thus, input 54 allows selection of the color of the lighted emitted, either red, from LEDs 44a–e when input 54 is in its first binary state, or near infrared, from LEDs 46a–e when input 54 is in its second binary state.

Amplifiers 78, 80, 82, and 84 are each a transistor, wired in an emitter-follower configuration. Depending on the states of inputs 54 and 56, only a single amplifier 78–84 will receive an input from oscillator 74 at any given time. Preferably resistor 96 will be selected such that its impedance is approximately twice that of resistor 94 and resistor 100 will be selected such that its impedance will be twice that of resistor 98. The outputs of amplifiers 78 and 80 are directed to current mirror 86 while the outputs of amplifiers 82 and 84 are directed to current mirror 88. The current which flows through transistor 102a will be roughly proportional to the current flowing through transistor 102c. Similarly, the current flowing through transistor 104a will be roughly proportional to the current flowing through transistor 104c. Accordingly, a greater current will flow through LEDs 44a–e when amplifier 78 is selected than when amplifier 80 is selected, and in a similar manner, more current will flow through LEDs 46a–e when amplifier 82 is selected than when amplifier 84 is selected. Thus, by manipulating inputs 54 and 56, microprocessor 50 can select a color of light, between red or near infrared, and can select, between two choices, the intensity of the light produced.

Preferably, oscillator 74 will produce a waveform which approximates a sine wave, thus having harmonic content substantially less than that of a square wave. When LEDs 44a–e and 46a–e are driven in this fashion, the electrical current flowing through the LED's will have a harmonic content far below that of a square wave current. Accordingly, the light produced by each individual LED 44a–e or 46a–e, will result in a modulated light beam having substantially less harmonic energy than would be produced if modulated with a square wave.

Referring now to FIG. 6, receiver 68 preferably comprises: a first amplifier 106 for amplifying a signal produced by direct light photodetector 48; a second amplifier 108 for amplifying a signal produced by reflected light photodetector 38; amplifier 114 providing ambient light compensation means for reducing the effects of ambient light on photodetector 38; analog selector 110 for selecting either the direct light signal or the reflected light signal as directed by input 70; and signal conditioner 112. Signal conditioning is generally known in the art and typically includes filtering and, if necessary, amplification of the signal. Signal conditioner 112 can also be thought of as a discriminator. Preferably signal conditioner 112 includes a second order band pass filter centered about 40 kilohertz. Since LEDs 44a–e and 46a–e are modulated at 40 kilohertz, signal conditioner 112 will discriminate between the signal resulting from the light produced by LEDs 44a–e and 46a–e and "noise" resulting from the signal produced by other light sources. As will be apparent to those skilled in the art, a variety of other methods, such as synchronous demodulation, are available to discriminate between the reflected, modulated light, and unwanted ambient light.

It should be noted that the light produced by LEDs 44a–e and 46a–e will contain a DC component if the signal from oscillator 74 (FIG. 5) is superimposed on a DC voltage. For the purposes of this invention, the steady-state light so produced is considered part of the ambient light and the low frequency affects of such light, particularly as the sensor height varies or from terrain variations, on reflected light detector 38 will also be compensated for by amplifier 114 and ultimately removed by signal conditioner 112.

In particular, amplifier 114 allows detector 38 to operate over a wider range of ambient lighting conditions without saturating. In addition, capacitors 116 and 118 AC couple the outputs of photodetectors 48 and 38, respectively, to eliminate DC offset voltages from the signals produced by detectors 48 and 38 which could otherwise cause the outputs of amplifiers 106 and 108 to saturate. In general, ambient light compensation means includes any of these techniques which reduce the degree to which ambient light may degrade or impede reception of the reflected light from light sources 44 and 46, or any other technique for improving the signal to noise ratio of the received signal.

Receiver circuit 68 provides output 72 which produces an amplified and filtered version of the signal received by one of the two detectors 38 or 48, as selected by input 70. The operation of analog to digital converter 58 is synchronized with the oscillator 74 so that conversions are performed on the peaks of the signal present at output 72.

In operation, the sensor is passed over crops such that modulated light from the emitter, both red and near infrared, is reflected back through the receiver lens and focused by the parabolic reflector onto the photodetector. The microprocessor 50 directs analog to digital converter 58 to read the received signal at the peaks of the waveform output by signal conditioner 112 for both the output of the reflected light detector 38 and the direct light detector 48. By calculating the ratio of the light reflected at each wavelength, i.e. the reflected intensity divided by the source intensity, the reflectance of the crop at each wavelength can be determined.

In a typical system, multiple sensors 20 will be used to scan a contiguous strip across one or more rows of plants. In such a system, microprocessor 50 receives synchronization timing information from a central source and uses that timing information to synchronize emission from emitter circuit 52. This process assures that light from adjacent sensors 20 are synchronized and consequently that such sensors do not interfere with each other. In a preferred method for synchronizing multiple units, microprocessor 50 includes a controller area network (CAN) interface. Such networks are well known in the art. To synchronize the emitters, a message is periodically transmitted on the network from the central source. Upon receipt of this message, each sensor sets the output of oscillator 74 to a known position in its periodic waveform, thereby synchronizing all sensors connected to the network.

Once the microprocessor 50 has gathered reflectance information from receivers 38 and 48, it is necessary to process the information to determine the need for nitrogen. One method for using reflectance information to determine such a need is disclosed in co-pending U.S. patent application, Ser. No. 09/911867, entitled "A Process for In-Season Fertilizer Nitrogen Application Based on Predicted Yield Potential," filed contemporaneously herewith, which is incorporated herein by reference.

To summarize the process, data from the sensor is used to predict the potential yield that can be achieved with additional, mid-growing season, nitrogen fertilization based on an in-season response index given by the equation:

$$YP_N = YP_0 * RI_{NDVI}$$

where:

$YP_N$ is the predicted or potential yield that can be achieved with additional fertilizer;

$YP_0$ is the predicted or potential yield based on growing conditions up to the time of sensing, that can be achieved with no additional nitrogen fertilizer;

$RI_{NDVI}$ is the In-Season-Response-Index computed as NDVI from Feekes 4 to Feekes 6 from a non-N-limiting fertilized strip divided by NDVI from Feekes 4 to Feekes 6 in the farmer's field fertilized in the common practice employed by the farmer, located adjacent to the non-N-limiting strip; and NDVI is the normalized difference vegetation index calculated as (NIR-red)/NIR+red) where NIR and red are reflectance values measured by the inventive sensor.

$YP_N$ can then be used to predict the percent of nitrogen (PNG) contained in the crop calculated as:

$$PNG = -0.1918 * YP_N + 2.7836 \ (PNG \ in \ \% \ N);$$

the predicted grain nitrogen uptake (GNUP) is calculated as:

$$GNUP = PNG * (YP_N/100);$$

the predicted forage nitrogen uptake (FNUP) calculated as:

$$FNUP_{NDVI} = 14.76 + 0.7758 e^{5.468 * NDVI};$$

and finally, the in-season mid-growing season fertilizer nitrogen requirement (FNR) is calculated as:

$$FNR = (GNUP - FNUP)/0.70 \ kg/ha.$$

As will be apparent to those skilled in the art, the above series of calculations may easily be performed in microprocessor 50 and FNR can then be used to control the rate of fertilizer application through a variable rate applicator 66.

Due to variations in various components employed in the inventive sensor, it may be desirable to provide a calibration procedure. Typically, the sensor may be calibrated by shining the emitter at an object having known reflectance properties and comparing the signal produced by photodetector 38 to an expected value. The response of the entire system may be determined independently for both red and near infrared and may be determined at each of the two selectable intensities. Constants may then be calculated and stored in non-volatile memory within microprocessor 50 for later use to correct subsequent measurements of plant reflectance.

One advantage of the present invention is that each individual sensor 20 may be independently calibrated. When multiple sensors are employed, for example along a boom, and each sensor has been properly calibrated, the amount of nitrogen available to each plant will be consistent throughout the field, regardless of which particular sensor scans any given plant.

Referring again to FIG. 5, emitter 52 can be adapted to output more light by adding additional LED's. Preferably, additional LEDs 44f–j and 46f–j would be driven by adding additional current mirror transistors 102b and 104b, respectively. In this way, the electrical current flowing through LEDs 44a–e would closely approximate the current flowing through LEDs 44f–j and similarly, the electrical current flowing through LEDs 46a–e would closely approximate the current flowing through LEDs 46f–j, resulting in consistent brightness throughout the individual LEDs of a given color. As will be apparent to those skilled in the art, additional groups of LEDs could be added to achieve any desired level of intensity. In addition, the number of red LED's 44 need not equal the number of infrared LEDs 46.

In a similar vein, it should also be noted that additional wavelengths of light may also be produced by sensor 20. A switch similar to switch 76 could be employed which provides the desired number of individual switches to accommodate the desired additional wavelengths of light. For each wavelength emitted, additional amplifiers, current mirrors, and LEDs are employed in the same configuration as those presently employed. Thus, the present invention is suitable for measuring the reflectance at any number of wavelengths.

Incorporating additional wavelengths of light allows the sensor to separate confounding factors from the estimate of nitrogen as well as increase the number of possible applications for the sensor. When more than two wavelengths of light are produced, it may be more practical to arrange the light emitting diodes into additional parallel rows with appropriately configured lenses such that the gap between individual LEDs of the same color does not become large enough to leave unilluminated holes in the field-of-view. For purposes of this invention, the parallel rows are viewed collectively as a single row having a width greater than one LED.

Figure 10:
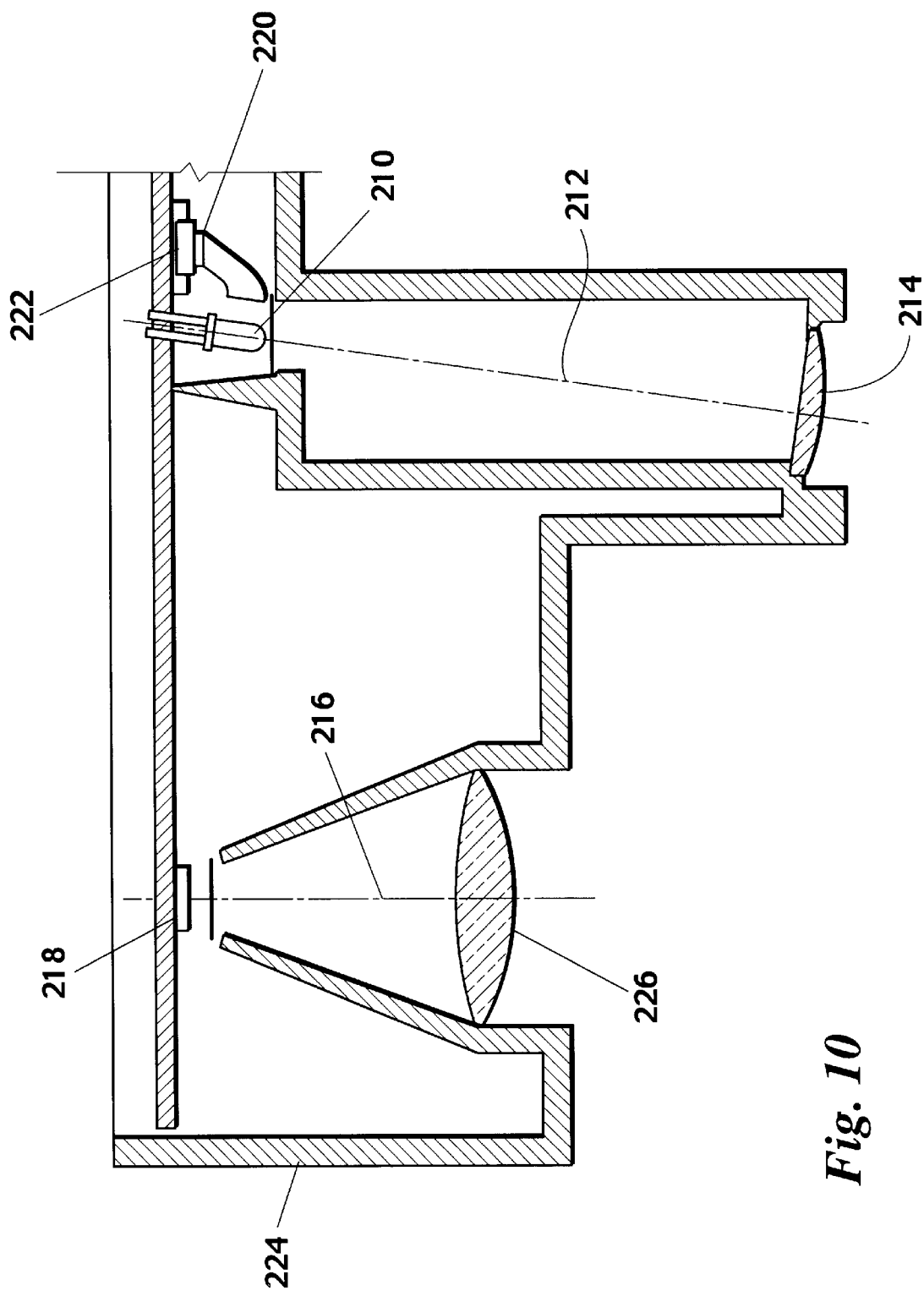
FIG. 10 provides a cutaway side view of an improved reflectance sensor.

As mentioned hereinbefore, prior art reflectance sensors are available to direct the selective application of herbicide to eliminate unwanted plants in a field. Features of the inventive sensor may be incorporated into such a prior art sensor to improve the performance of such a sensor and to adapt such a sensor for use in the application of other farming products. For example, the sensors described in U.S. Pat. No. 5,763,873 issued to Beck et al., which is incorporated herein by reference, and U.S. Pat. No. 5,789,741 issued to Kinter et al., likewise incorporated herein by reference, could easily be adapted to house the inventive circuitry. As shown in FIG. 10, light source 210 directs a beam of light, as indicated by line 212, through lense 214 towards a target. Light reflected by the target, as indicated by line 216, is focused by lense 226 on to reflected light photodetector 218. In accordance with the present invention, a portion of the light emitted from all of the emitters which collectively comprise light source 210 is collected by light pipe 220 and directed to direct light photodetector 222. While mechanically, sensor 224 differs from sensor 20 (FIG. 2), the circuitry employed therein may be identical, resulting in a sensor which provides improved accuracy in regard to the measured reflectance over the prior art design and which is, therefore, suitable for purposes beyond the selective application of herbicide.

As will be apparent to those skilled in the art, the inventive sensor 20 may be scaled upward or downward in size to achieve virtually any desired resolution. Thus, while the preferred embodiment is suitable for sites of approximately four square feet, the invention is not so limited. With presently available light sources and detectors, a resolution of less than 12 square inches per site is possible.

It should also be noted that, while the inventive sensor can provide an output to directly control the rate of application of fertilizer, it could also be used to create a prescription map for later application of fertilizer. In such a system, positional information is obtained from a GPS receiver, from the vehicle carrying the sensor, or from some other position indicating system. Crop conditions are stored in nonvolatile memory in such a manner that the condition at each specific site within the field may be later recalled for use in developing a prescription map.

Figure 8:
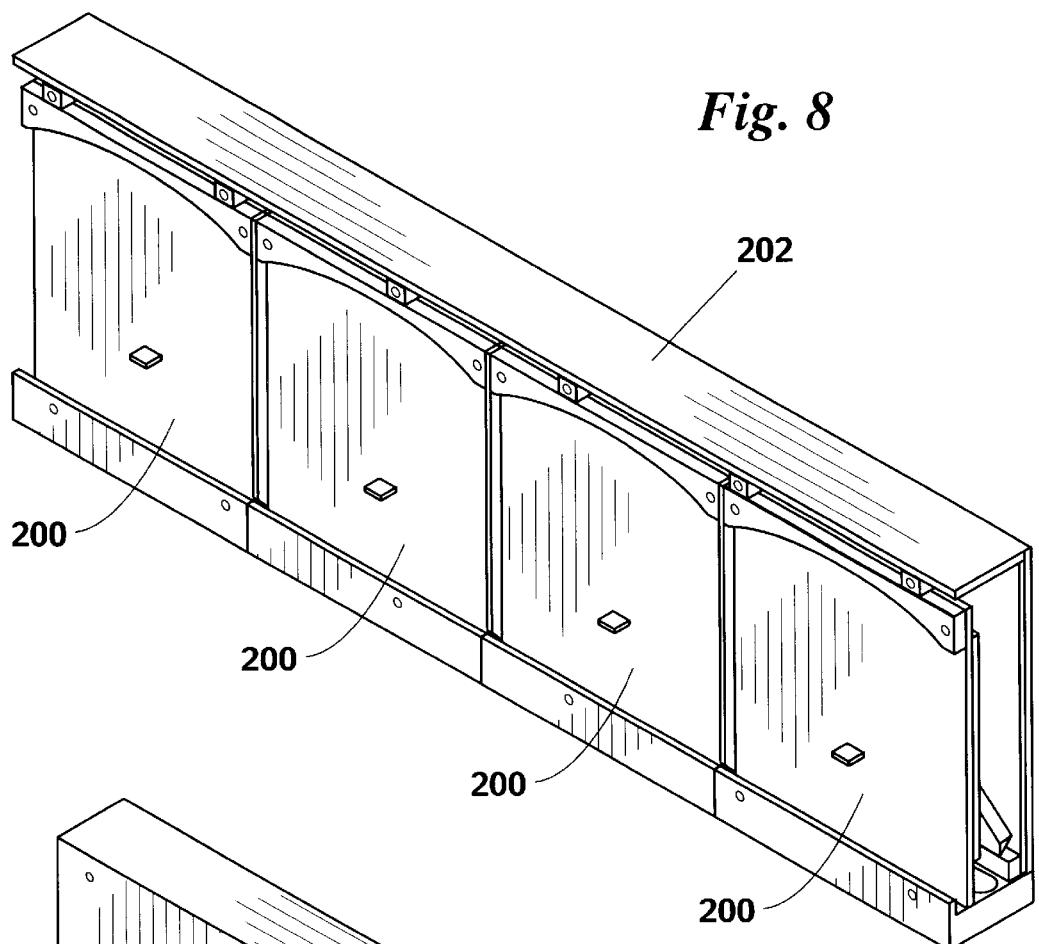
FIG. 8 provides a cutaway perspective view of a preferred multiple sensor embodiment of the inventive reflectance sensor.
Figure 9:
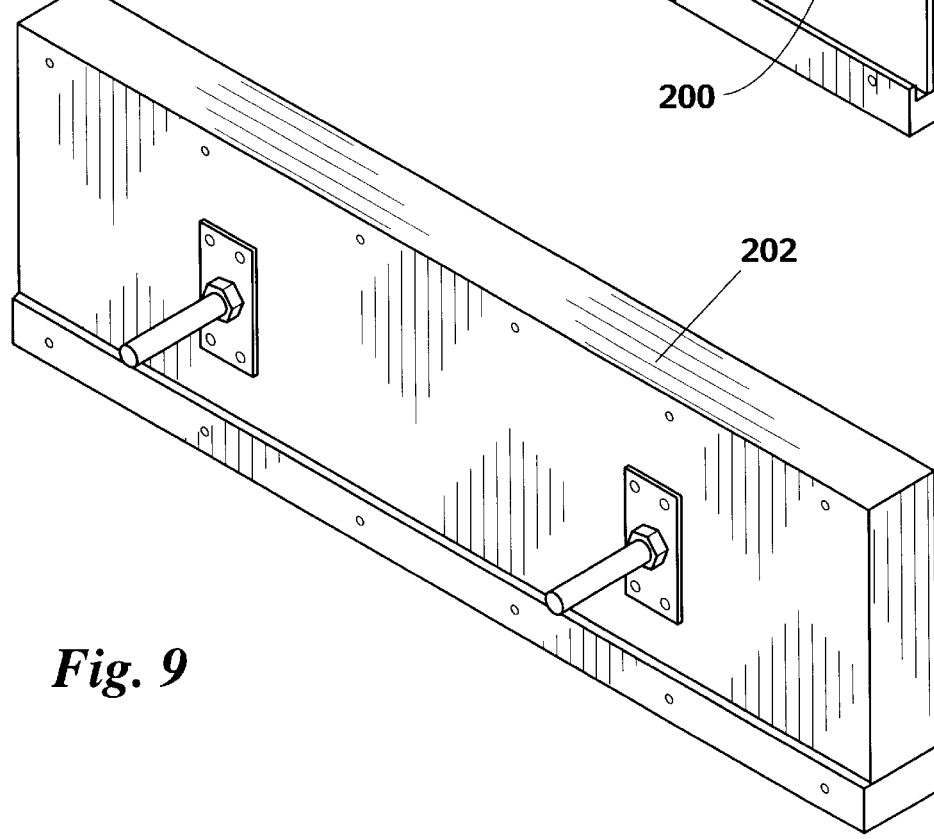
FIG. 9 provides a perspective view of the multiple sensor embodiment.

It should be further noted that multiple sensors 200 may be incorporated into a single housing 202 as shown in FIGS. 8 and 9. Typically, each sensor 200 would be constructed in accordance with the description of sensor 20 and have its own microprocessor for performing the calculations to arrive at the required mid-growing season fertilizer. This arrangement is particularly well suited for a use on a spray boom where, ideally, sensors are aligned, end-to-end along the boom. Optionally, instead of directly controlling a variable rate applicator, the sensors may provide reflectance data or growing conditions to a central computer via a communication network, such as a CAN network. The central computer would both direct an array of variable rate applicators and create a log of crop conditions throughout the field for later analysis or to create a history for comparison with those of other growing seasons.

In a multiple sensor configuration, it is also possible for a single microprocessor to control multiple sensors. When multiple sensors are controlled by a single processor, or when sensors are interconnected via a network, and the resolution is reduced, it is possible to perform image processing within an individual sensor to determine such factors as: missing plants; non-uniform plant stands; chlorophyll concentration; infestation of disease or pests; changes in soil background; etc. In addition, networking of the individual sensors allows conditions to be averaged over a larger area for applications where a larger site is desired and networking enables microprocessor controllers to use information collected from sensors not under their direct control to make treatment decisions.

Through the proper selection of resolution and appropriate use of reflectance information from various wavelengths of light, the inventive sensor can be used to simultaneously detect and treat multiple anomalies in a single pass over a field. For example, using the techniques described in U.S. Pat. No. 5,789,741 issued to Kinter, previously incorporated herein by reference, the inventive sensor could be used to selectively apply nitrogen at an optimal rate to desirable plants while also selectively applying herbicide between plant rows to eliminate unwanted weeds.

Finally, it should likewise be noted that, while farming applications of the inventive sensor were discussed in relation to the preferred embodiment, the invention is not so limited. The inventive device could be used to improve the efficiency of plant maintenance in virtually any application, i.e. golf courses, lawn care, landscape maintenance; etc. While the constants in the equations given above may vary from crop-to-crop, the inventive method is otherwise applicable to virtually any type of plant.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A spectral reflectance sensor for determining the reflectance of a plant comprising:
   a housing;
   a light source housed in said housing, said light source projecting light of a predetermined wavelength;
   a reflected light receiver including:
     a first photodetector positioned to receive reflected light originating from said light source
     ambient light compensation means for reducing the effects of ambient light on said first photodetector; and
     a first output;
   a direct light receiver including:
     a second photodetector positioned to receive incident light from said light source; and
     a second output;
   a discriminator for distinguishing the light originating from said light source and reflected by a plant from ambient light; and
   a microprocessor having an input for reading said first output and an input for reading said second output,
     wherein the reflectance at said predetermined wavelength is proportional to the quotient of the value of said first output divided by the value of said second output.

2. The spectral reflectance sensor of claim 1 wherein said light source is a first light source and said predetermined wavelength of light is a first predetermined wavelength of light and the reflectance sensor further comprises:
   a second light source housed in said housing, said second light source projecting light of a second predetermined wavelength.

3. The spectral reflectance sensor of claim 2 further comprising:

a selector in communication with said microprocessor wherein said microprocessor can select either said first light source to emit light or said second light source to emit light, wherein said microprocessor can measure the reflectance at said first predetermined wavelength independently of the reflectance at said second predetermined wavelength of light.

4. The spectral reflectance sensor of claim 3 wherein said first light source produces red light of a predetermined wavelength and said second light source produces near infrared light of a predetermined wavelength and wherein said microprocessor calculates NDVI based on the reflectance computed while red light is emitted and the reflectance computed while near infrared light is emitted.

5. The spectral reflectance sensor of claim 1 wherein said light source is a first light source of a plurality of light sources and each light source of said plurality of light sources produces light at a predetermined wavelength different from the wavelength of each of the other light sources of said plurality of light sources.

6. The spectral reflectance sensor of claim 5 wherein each light source of said plurality of light sources comprises a plurality of light emitting diodes.

7. A normalized difference vegetation index sensor comprising:

a first light source which emits a modulated beam of red light;

a second light source which emits a modulated beam of near infrared light;

a first receiver for receiving reflected light produced by said first light source and said second light source, said receiver having a first output;

a second receiver for receiving incident light from said first light source and said second light source, said second receiver having a second output;

a signal conditioner responsive to the modulation of said modulated beam such that said signal conditioner can discriminate between said first or second light sources and ambient light, said signal conditioner having a first input for receiving said first output or said second output and said signal conditioner having a third output;

a microprocessor having a second input for receiving the output of said signal conditioner such that said microprocessor can determine the intensity of said first light source, the intensity of said second light source, the intensity of the reflected light received from said first light source; and the intensity of the reflected light received from said second light source, wherein said microprocessor provides an output indicative of the normalized difference vegetation index calculated from the intensities determined from the signal at said second input.

* * * * *